United States Patent [19]

Sundrehagen et al.

[11] Patent Number: 5,631,364
[45] Date of Patent: May 20, 1997

[54] LABELLED BORONIC ACID DERIVATIVES

[75] Inventors: Erling Sundrehagen, Oslo; Frank Frantzen, Tverlandet, both of Norway

[73] Assignee: AXIS Biochemicals ASA, Norway

[21] Appl. No.: 220,525

[22] Filed: Mar. 31, 1994

[51] Int. Cl.$^6$ ...................................................... C07F 5/02
[52] U.S. Cl. .............................. 540/128; 544/69; 546/13; 548/110; 548/405; 549/4; 549/213; 552/10; 562/7
[58] Field of Search ............................. 540/128; 544/69; 546/13; 548/110, 405; 549/4, 213; 552/109; 562/7

[56] References Cited

U.S. PATENT DOCUMENTS

| | | | |
|---|---|---|---|
| 4,496,722 | 1/1985 | Gallop et al. | 544/69 |
| 4,861,728 | 8/1989 | Wagner | 436/501 |
| 5,242,842 | 9/1993 | Sundrehagen et al. | 436/536 |

FOREIGN PATENT DOCUMENTS

| | | |
|---|---|---|
| 3720736 | 1/1989 | Germany. |
| WO9013818 | 11/1990 | WIPO. |

OTHER PUBLICATIONS

Koyama; Chemical Abstracts; 114:118100h, 1990.

*Primary Examiner*—Richard L. Raymond
*Attorney, Agent, or Firm*—Bacon & Thomas

[57] ABSTRACT

The invention provides novel labelled boronic acid conjugates of formula

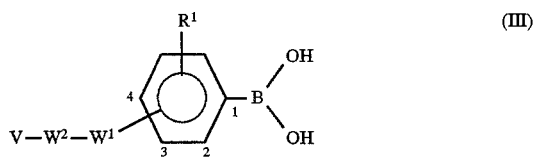

(wherein V is a reporter moiety;

$W^2$ is a bond or an organic linker moiety;

$W^1$ is a *$SO_2NR^2$, *$CON^2$ or *$CH_2N{\oplus}R^2{}_2$ group bound at the *-marked atom to the phenyl ring;

$R^1$ is hydrogen or an electron withdrawing substituent group; and each $R^2$ independently is hydrogen or an optionally hydroxylated and optionally $C_{1-6}$-alkoxylated $C_{1-6}$-alkyl group) and salts thereof, e.g. for use in assays for cis-diols such as glycated blood proteins, having enhanced water-solubility and storage stability.

17 Claims, No Drawings

LABELLED BORONIC ACID DERIVATIVES

FIELD OF THE INVENTION

The present invention relates to novel boronic acid derivatives carrying a reporter species or "label".

BACKGROUND OF THE INVENTION

Particularly in diagnostic medicine it is well established practice to use labelled species to bind to substances of interest (analytes) in order that the intensity of the original from the lable may be used to ascertain the presence or concentration of the analyte.

Such labelled species require two functional attributes—the first being the ability to produce a detectable signal, actively or passively, and the second being the ability to bind to a desired binding partner.

The signal forming attribute may conveniently be fulfilled by the presence in the labelled species of a reporter moiety or "label" which itself acts as a radiation emitter, absorber or modifier or which cooperates with another species to achieve a radiation emitting, absorbing or modifying effect. Thus for example the label may be a chromophore, a fluorophore, a radionuclide, or a material having detectable magnetic characteristics, e.g. paramagnetism, superparamagnetism etc.

One form of labelled species that has been proposed for diagnostic use, e.g. in assay lists, fulfills the binding ability attribute by the inclusion in the species a —B(OH)$_2$ or —B(OH)3—binding group.

Such boronic acid conjugates have the ability to bind to cis-diols, e.g. in proteins. By way of example, boronic acid conjugates of this nature are described in WO-92/08722, US-A-4659817, DE-A-3720736 and US-A-4861728. The compounds described there comprise antibody or chromophoric or fluorophoric label moieties. Such compounds are useful in assays for glycated blood proteins in view of their ability to bind to the glycosyl moieties. The labelled conjugates of WO-92/08722 are especially useful in this regard as the chromophores and fluorophores there described have absorption maxima above 600 nm and thus there is no interference between their spectral response and that of hemoglobin.

These labelled boronic acid conjugates can be represented by the general formula I

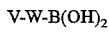

V-W-B(OH)$_2$      (I)

where V is a reporter moiety, e.g. a chromophore, fluorophore or radioisotope and W is a bond or linking organic group.

WO-92/08722, like other publications describing labelled boronic acid conjugates, suggested that the linker group, W in formula I above, might suitably incorporate a m-aminophenyl group attached to the boronic acid residue. Thus such compounds may readily be prepared by conjugating the label to m-aminophenyl-boronic acid thereby producing a compound of formula II

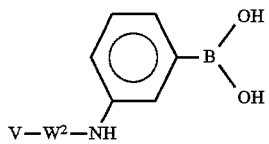

(where V is as defined above and W$^2$ is a bond or an organic linker moiety).

Such compounds however have been found to have limited acceptability in terms of stability and water solubility and for certain assay procedures have necessitated the use of organic co-solvents such as DMSO, DMF and formamide rather than of water alone.

SUMMARY OF THE INVENTION

It has now been found that by replacement of the carbonylamino-1,3-phenylene linker group previously used, labelled boronic acid conjugates having improved stability and improved water solubility may be obtained.

Thus viewed from one aspect the invention provides labelled boronic acid conjugates of formula III

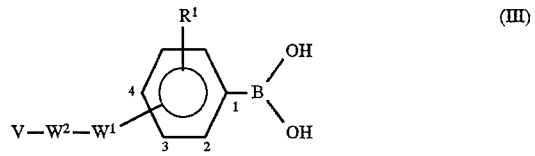

(where V is a reporter moiety;

is a bond or an organic linker moiety;

W$^1$ is a *SO$_2$N$^2$, *CON$^2$, or, less favorably, a *CH$_2$N⊕$^2$$_2$ group attached at the * marked atom to the phenyl ring;

R$^1$ is an electron withdrawing functional group, e.g. a SO$_2$H, COOH or NO$_2$ group; and each R$^2$ independently is hydrogen or optionally hydroxylated, optionally C$_{1-6}$-alkoxylated C$_{1-6}$-alkyl) and salts thereof.

DETAILED DESCRIPTION

The new compounds have reduced pKa, better water-solubility and increased stability in aqueous solution than the analogous m-aminophenyl-boronic acid conjugates.

Since it is generally accepted that it is the anionic form of the boronic acid that participates in the cis-diol esterification, the lower pKa is advantageous insofar as it permits a lower pH to be used in the coupling reaction with the cis-diol analyte while maintaining a sufficiently high concentration of the dissociated boronic acid. This is particularly advantageous in blood assays where zinc ions are used to precipitate hemoglobin due to the increased stability of the zinc ions at the lower pH. At alkaline pH's zinc has a tendency to produce unwanted insoluble hydration complexes.

Previously this problem has had to be addressed by inclusion of further complexing agents which stabilize the zinc until the hemoglobin is added. Such agents must of course form weaker complexes with zinc than does hemoglobin itself in order to allow the zinc to effect hemoglobin precipitation. Thus, the reduction of the pH of the solution of labelled boronic acid and zinc, ideally to about 7 to 8, is made possible by the lower pKa of the boronic acid and facilitates the balance of complexing agents needed to stabilize the zinc.

To enhance pKa reduction and improve boronic acid stability in the compounds of formula III, it is especially desirable to have the phenyl ring substituted by one or more electron withdrawing substituents R$^1$. Most effectively such substitution is at the ortho or para positions relative to the boronic acid residue. Moreover in those compounds of the invention where W$^1$ is attached to the phenyl ring via a heteroatom or an unsaturated carbon, attachment is desirably at the para position while for the CH$_2$ attached moieties attachment is preferably at the meta or para positions.

The precise chemical nature of the VW² moiety is of secondary importance—its primary function is simply to provide a reporter moiety (i.e. a label) and means for attaching that label to the W¹ moiety.

Nonetheless, certain W² linker moieties have been found to be particularly suitable for use in this regard and in this context mention may be made of optionally substituted aza and/or oxa-alkylene groups, e.g. groups of formula IV

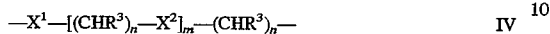

(wherein each n is independently an integer of 1 to 6 preferably 2 or 3, especially 2;

m is 0 or a positive integer, e.g. 1 to 5, m preferably being 0, 1 or 2;

X¹ is a bond, an oxygen or sulphur atom, a NR² group, or a carboxy or carbonyl group or the residue of any other functional group serving to link W² to V, X¹ preferably being a group NR²;

each X² is independently an oxygen or sulphur atom or an NR² group, X² preferably being O or N²;

each R³ independently is hydrogen, hydroxy, formyl, carboxy, or optionally hydroxylated and/or $C_{1-6}$-alkoxylated $C_{1-6}$-alkyl, or a group CHR³ may represent a carbonyl group, however is preferably hydrogen on all but one of the carbons of any $(CH^3)_n$ moiety, being hydrogen, hydroxy or carboxy on the remaining carbons; and each alkyl or alkylene moiety, unless otherwise stated conveniently contains 1 to 6, especially 1 to 3 carbons) optionally in anionic, cationic, or zwitterionic form. In such a linker moiety the $(CH^3)_n$ moiety remote from X¹ is attached to the W¹ moiety and the group X¹ is coupled to the label V.

Examples of such groups of formula IV include but are not limited to the following:

—NH—CH₂—CHOH—CH₂—
—NH—CH₂CH₂—NH—CH₂CH₂—
—NH—CH₂CH₂—O—CH₂CH₂—
—NH—CH₂CH₂—
—NH—CH₂CH₂CH₂—
—NH—CH₂CH₂CH₂CH₂—
—NH—CH₂CH₂CH₂CH (COOH) —
—NH—CH₂CHOH—
—NH—CH₂CH(COOH)—
—NH—CH₂—NH—CH₂—
—NH—CH₂CH₂CH₂CH₂CH₂CH₂—
—NH—CH₂CH₂CH₂CH₂CH₂—
—NH—CH₂—O—CH₂—
—NH—CH₂—O—CH₂—O—CH₂——NH—CH₂CH₂—O—CH₂CH₂—O—CH₂CH₂—
—NH—CH (COOH) CH₂CH₂—
—NH—CH (COOH) CH₂CH₂CH₂—
—NH—CH₂CH(COOH)CH(COOH)—
—NH—CH₂CHOHCHOH— and
NH—CH₂CH(CHO)CH(CHO) —

However other spacer groups having functional groups appropriate for attachment to label moieties, e.g. nitrile, halide, epoxide, carbonyl, carboxyl, amine, phosphonate and sulphonyl groups may of course be used, especially where they also serve to enhance water solubility.

The reporter moiety, as mentioned above, may be any moiety capable of producing an assessable signal. Generally however chromophores and fluorophores, e.g. azine, triarylmethine, phthalocyanine and cyanine dyes, will be preferred for reasons of ease of assessment, safety, efficacy and expense. Particularly preferred for labelled agents for use in blood assays will be compounds in which the chromophore or fluorophore has an absorption maximum in the range 600–1000 nm, especially those triphenylmethine dyes which have this characteristic.

In preferred embodiments, the conjugates of the invention are of formulae V, VI or VII

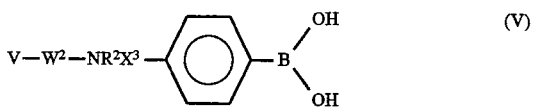

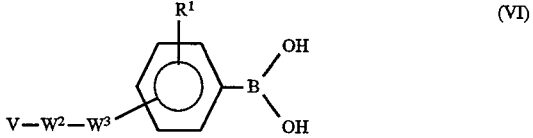

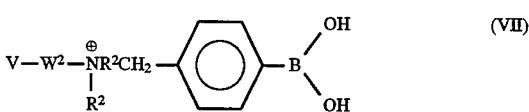

(where X³ is CO or SO₂;

W³ is NHCO or SO₂NH; and R¹ is hydrogen or, preferably, an electron withdrawing group, e.g. SO₂H, COOH or NO₂) and salts and complexes thereof.

In formulae V to VII, linker groups W² are preferably of formula IV and especially preferably carry at least one solubilizing (hydrophilic) group. In the compounds of formula VI, the R¹ group is preferably in an ortho or para position and the VW²W³ group in a meta or para position, in each case relative to the B(OH)₂ group.

The labelled compounds of the invention may be prepared by coupling a reporter moiety to a substituted phenylboronic acid optionally using a further reagent to provide the whole or part of the linker group between the phenylboronic acid and the reporter moiety. Particularly conveniently however, the labelled compounds of the invention are produced by coupling a reporter molecule to a linker-substituted phenylboronic acid of formula VIII

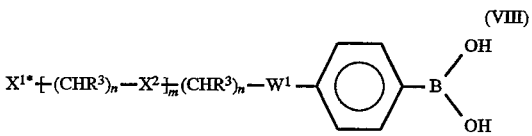

(where X², R¹, R³, n, m and W¹ are as defined above and X¹ is a functional group reactive to couple to a reporter molecule, e.g. a leaving group such as a halide, or an acid or activated acid group, such as a carboxyl group, or an amine, hydroxyl or thiol group). The compounds of formula VIII and salts thereof form a further aspect of the invention.

The coupling of the reporter molecule to phenylboronic acids can be achieved using conventional chemical techniques starting from reagents which are commercially available or are known from the literature. Similarly the compounds of formula VIII may be prepared by conventional chemical techniques starting from such known compounds as aminophenylboronic acids, methylphenylboronic acids etc. Exemplary reaction schemes are set out below:

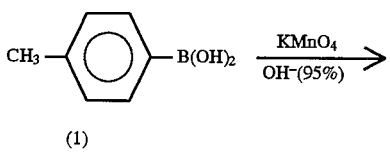

(1)

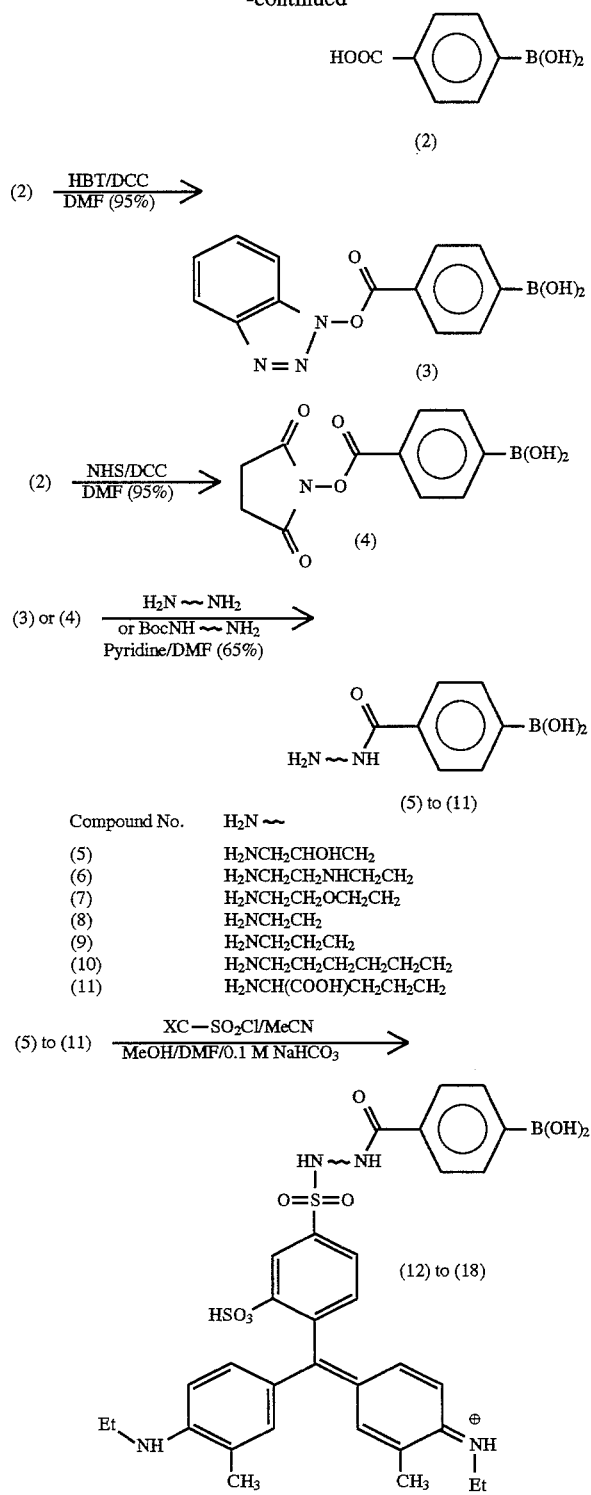

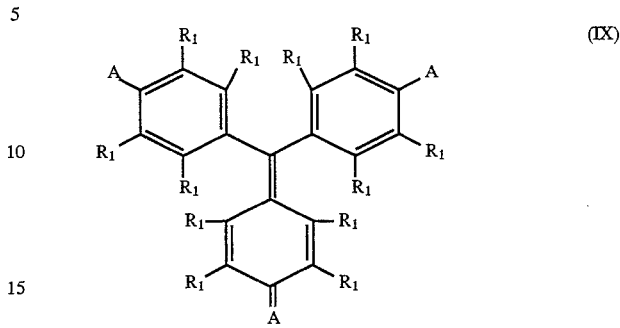

In the reaction scheme set out above, the reporter molecule coupled in the production of compounds 12 to 18 is a cyanine dye. While for the purposes of glycated blood protein assays such dyes are preferred, especially where they have fluorescence absorption maxima above 600 nm, other reporter moieties may be used particularly for other assay procedures. Examples of suitable reporter moieties are described for example by Axis Biochemicals AS in WO-92/08722, by Gallop in US-A-4496722, by Wagner in US-A-4861728, by Schleicher in DE-A-3720736, by Pease in US-A-4830786.

Particularly preferred are triarylmethine dye, e.g. a triphenylmethine dye such as those of formula IX in which each $R_1$ independently represents a hydrogen atom, an organic group or a (preferably hydrophilic) substituting group (e.g. hydroxy, carboxy, sulpho or chlorosulphonyl), and at least two of the A groups represent auxochrome groups, any non-auxochrome A group being as defined for $R_1$. Preferred auxochrome groups include amine/imine systems as represented by $N(R)_2/N^+(R)_2$ and NHR/$N^+$HR systems (where each R represents an organic group, e.g. as described below for $R_1$, preferably a lower alkyl group such as methyl or ethyl), alone or in combination with O/OH. The linker-phenylboronic acid moiety may, for example, be attached to one of the phenyl rings, e.g. coupled via a group such as carboxy or sulpho, or to one of the R groups in an amine/imine auxochrome system. It will be appreciated that the other resonance structures and enantiomers which may be drawn are also intended to be within the scope of formula IX.

Where any $R_1$ represents an organic group this may, for example, be selected from alkyl, alkenyl and alkynyl groups, e.g. containing up to 6 carbon atoms, such as methyl, ethyl, n-propyl, isopropyl, n-butyl, sec-butyl, t-butyl, vinyl, allyl, ethynyl or propargyl; cycloalkyl or cycloalkenyl, e.g. containing 5–7 carbon atoms, such as cyclopentyl, cyclohexyl, cycloheptyl, cyclohexenyl or cyclopentadienyl; aryl groups, e.g. containing 6–12 carbon atoms, such as phenyl, tolyl or naphthyl; heterocyclic rings, e.g. 5–7 membered saturated and unsaturated rings containing at least one heteroatom selected from oxygen, nitrogen and sulphur, such as furyl, thienyl, pyridyl, pyrimidyl, pyridazyl, thiazolyl, thiazinyl, triazinyl, pyrrolyl, imidazolyl, pyrazolyl, pyrrolidinyl, piperidinyl, piperazinyl or morpholinyl; lower (e.g. $C_{1-4}$) alkyl substituted by any of the previously described cycloalkyl, cycloalkenyl, aryl or heterocyclic groups; any of the previous groups interrupted and/or substituted by one or more heteroatoms, e.g. so as to contain one or more ether, thioether, amino, amido, carbonyl or thiocarbonyl groups; or any of the previous groups carrying one or more substituents which may, for example, be selected from hydroxy, mercapto, amino, halo, nitro, azido, carboxy, cyano and isothiocyanato, or any other substituent compatible with the boronic acid residue. Indeed in general in the compounds of the invention, unless otherwise specified, alkyl, alkenyl and alkenylene moieties will contain up to 6 carbon atoms and cyclic groups will have 5 to 7 membered rings.

Although the absorption maxima of dyes derived from compounds of formula IX are normally below 700 nm, some derivatives may also possess absorption in the near infrared area. Examples of such compounds are those derived from compounds of formula IX where two or more of the phenyl groups are further linked, e.g. by a bond or a bridging group, to form a further at least five membered ring. Examples of such dyes include those in which the label is derived from a compound of formula X

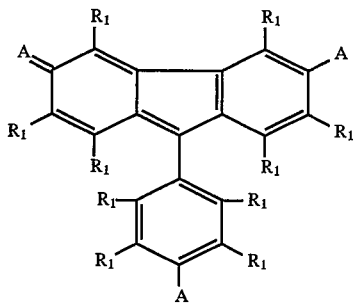

where $R_1$ and A are as defined above. Absorption maxima for such dyes and the size of the bathochromic shift depends on the auxochrome groups present in such derivatives. Compared to Crystal Violet (A/A/A =$NMe_2$/$NMe_2$/$NMe_2$) and Malachite Gren (A/A/A=$NMe_2$/$NMe_2$/H), such bridging displaces the longest absorption band to longer wavelength, resulting in absorption at 850 nm and 955 nm, respectively. Even greater bathochromic shifts can be produced using acetylenic analogues of triphenylmethine dyes of formula XI

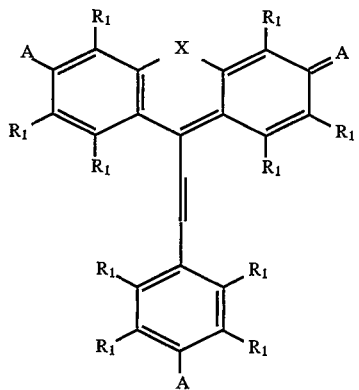

(where X is a bond or a linking atom or group, e.g. oxygen, nitrogen, sulphur or carbon substituted according to valence demands, e.g. with protons or organic groups). Thus X may be $C(R_1)_2$ where $R_1$ is for example an alkyl group).

In formula XI, the resonance system is further increased (by greater delocalization of the positive charge) by the triple bond as well as the bridging of the phenyl rings.

These derivatives often possess several absorption bands in the near infrared wavelength area and distinct absorption bands are seen around 1000 nm.

Another particularly useful category of compounds according to the invention includes those in which V is derived from a cyanine or mercyanine dye, e.g. as represented by formulae XII and XIII respectively

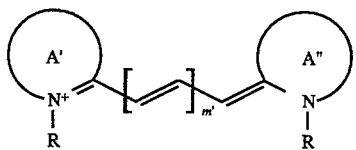

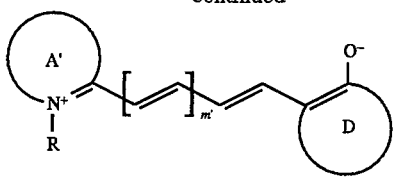

and the corresponding alternative resonance structures. In the above formulae A' and A" represent quaternized heterocyclic bases or heterocyclic aromatic groups containing ring oxygen and/or sulphur atoms; D represents a ketomethylene-derived nucleus; R is as hereinbefore defined; and m' is an integer, e.g. of 1–3, conveniently 2 or 3.

The analogous compounds wherein the terminal A' and A" rings are attached at carbons adjacent ring oxygen or sulphur atoms instead, i.e. the structural isomers of formulae XIV and XV are also suitable

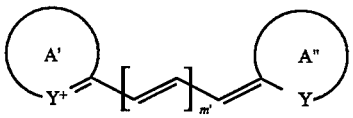

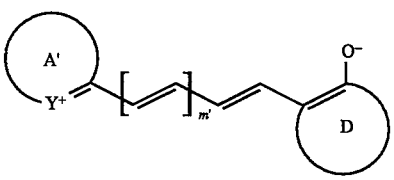

(where R, m', A', A" and D are as defined above and Y is O or S).

Examples of dyes of this type include those of formula XVI

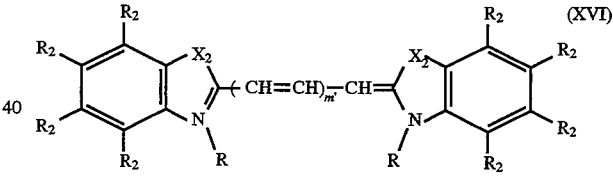

in which m' and R are as hereinbefore defined, $X_2$ represents a heteroatom such as oxygen or sulphur or an optionally mono- or di-substituted methylene group, and each $R_2$ independently represents a hydrogen atom, an organic group (e.g. as hereinbefore described for $R_1$) or a (preferably water-solubilizing) substituting group, or adjacent $R_2$ groups may together with the carbon atoms to which they are attached form fused monocyclic or polycyclic ring systems. Water-solubility enhancing substituents are desirably present as one or more of $R_2$, one preferred such substituent being carboxymethyl, which will conjugate to amine-containing molecules such as m-aminophenyl boronic acid with little or no change in the absorption characteristics of the cyanine chromophore. The extensive conjugation seen in these molecules can increase their chemical/photochemical instability, but appropriate dye design, for instance incorporating the polymethine chain into one or more cyclic structures is possible. Examples of such dyes are {4-[7-(2-phenyl-4H-1-benzothiopyran-4-ylidene )-4-chloro-3,5-trimethylene-1,3,5-heptatrienyl]-2-phenyl-1-benzothiopyrilium perchlorate}, and 3,3'-diethyl-9,11,15,17-dineopentylene-thiapentacarbocyanine perchlorate.

The labelled boronic acid conjugates of the invention can be prepared by reacting an appropriately functionalized reporter molecule having the desired reporter characteristics, e.g. spectral characteristics, to couple it to the desired phenylboronic acid residue as described above.

The labelled conjugates of the invention may be used in diagnostic test procedures, e.g. the glycated blood protein assays of WO-92/08722 and WO-90/13818, and this use and diagnostic kits therefor comprise further aspects of the invention.

Thus viewed from a further aspect the invention provides the use of a labelled boronic acid compound of formula III or a salt thereof in an assay procedure, suitably a diagnostic assay, especially a blood assay.

Viewed from a yet further aspect the invention also provides an assay kit comprising a compound of formula III or a salt thereof, means for contacting a cis-diol containing fluid sample with said compound, means for separating labelled, cis-diol conjugates thus formed and optionally means for assessing said separated conjugates.

Thus the assay kit may conveniently comprise a solution (e.g. a zinc containing aqueous solution buffered to pH 6.5 to 8, preferably 7 to 7.5) of a compound of formula III or salt thereof, a mixing vessel and a porous web (e.g. filter paper) capable of retaining the labelled cis-diol conjugates. Optional assessment means may conveniently comprise a spectrophotometer appropriately arranged to detect light emitted by (or modified by) the label.

The following non-limiting Examples are provided to illustrate the invention further:

Example 1: 4-Carboxy-phenylboronic acid (CPBA)

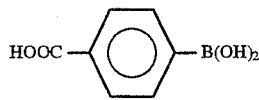

4-Methyl-boronic acid (5g, 0.037 mol) was dissolved in 300 ml 0.25 M NaOH using a magnetic stirrer. After 10 minutes, a suspension of $KMnO_4$ (12.3 g, 0.078 mol in 130 ml water) was added and the solution was left to react overnight (approx. 12 hours) at ambient temperature. The solution was then heated to 60° C. and hot-filtered and the filter subsequently washed with 2×50 ml hot water. The filtrate was then reduced to ⅓ volume, heated to 60° C. and finally made slightly acidic by adding concentrated hydrochloric acid before cooling. White needle-like crystals were collected in 75% yield.

Example 2:4-Benzotriazolyloxycarbonyl-phenylboronic acid (HBT-CPBA)

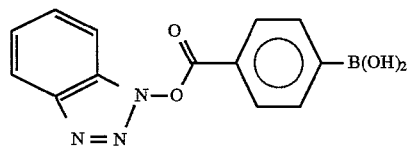

To a solution of 4-carboxy-phenylboronic acid (CPBA, Example 1, 2 g, 0.0121 mol) in N,N-dimethylformamide (DMF) was added 1-hydroxybenzotriazole (HBT, 2.04 g, 0.0151 mol) and N,N'-dicyclohexyl-carbodiimide (DCC, 4.98 g, 0.024 mol) both dissolved in DMF (the total volume was 170 ml DMF). The solution was left to react overnight (approx. 12 hours) under a nitrogen atomosphere and at ambient temperature, and then filtered to remove the insoluble urea byproduct (DCU). The title compound was used in subsequent reactions without further purification.

Example 3: 4-Succinimidyloxycarbonyl-phenylboronic acid (NHS-CPBA)

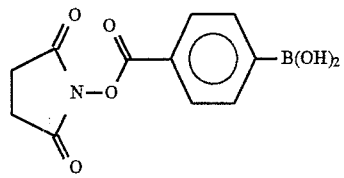

4-Carboxyphenyl-boronic acid (CPBA, Example 1, 0.25 g, 1.51 mmol) and N-hydroxysuccinimide (0.26 g, 2.26 mmol) were dissolved in 8.5 ml DMF using a magnetic stirrer. 20 ml of dichloromethane ($CH_2Cl_2$) was then added, and the solution was stirred for 10 minutes. N,N'-dicyclohexyl-carbodiimide (DCC, 0.93 g, 4.52 mmol) in 3 ml $CH_2Cl$ was then added. The solution was left to react under a nitrogen atmosphere overnight (approx. 12 hours) at ambient temperature, and then filtered to remove the insoluble urea byproduct (DCU). The title compound was used in subsequent reactions without further purification.

Example 4:4-((3-Amino-2-hydroxypropyl) aminocarbony1)-phenylboronic acid (CPBA-DAPOL)

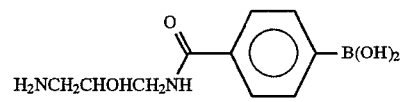

A newly filtered solution of HBT-CPBA (Example 2, 0.0121 mol) was added through a dropping funnel to a solution of 1,3-diamino-2-propanol (DAPOL, 1.09 g, 0.0121 mol) in 15 ml pyridine. The mixture was stirred under nitrogen and left to react at ambient temperature overnight (approx. 12 hours). The product was isolated and purified by chromatography on silica gel eluting with methanol:$NH_3$ (aq), 1:0.5. The title compound was isolated as matt white plate-like crystals.

Example 5: 4-((3-Amino-2-hydroxypropy1) aminocarbonyl)-phenylboronic acid (CPBA-DAPOL)

The procedure of Example 4 was repeated using a newly filtered solution of NHS-CPBA (Example 3, 0.0121 mol) instead of HBT-CPBA.

Example 6:4-((3,6-Diaza-hex-1-yl)aminocarbonyl)-phenylboronic acid (CPBA-BAEA)

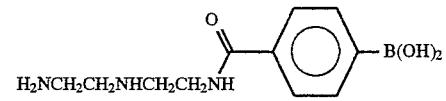

A newly filtered solution of HBT-CPBA (Example 2, 0.00121 mol) was added through a dropping funnel to a solution of bis-(2-aminoethyl)-amine (BAEA, 0.00133 mol) in 1.5 ml pyridine. The mixture was stirred under nitrogen and left to react overnight (approx. 12 hours) at ambient temperature. The title compound was isolated and purified by chromatography on silica.

Example 7: 4-((3,6-Diaza-hex-1-yl)aminocarbonyl) phenylboronic acid (CPBA-BAEA)

The procedure of Example 6 was repeated using a newly filtered solution of NHS-CPBA (Example 3, 0.00121 mol) instead of HBT-CPBA.

Example 8: 4-(5-Amino-3-oxapent-1-yl) aminocarbonyl)phenylboronic acid (CPBA-BAEE)

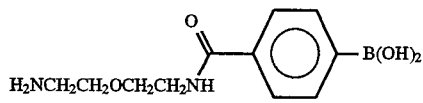

A newly filtered solution of HBT-CPBA (Example 2, 0.00121 mol) was added through a dropping funnel to a solution of bis-(2-aminoethyl)-ether (BAEE, 0.00106 mol) in 10 ml of 0.4M sodium-bicarbonate buffer, pH 8.5. The mixture was stirred and left to react overnight (approx. 12 hours) at ambient temperature. The reaction mixture was evaporated to dryness and the title compound isolated and purified by chromatography on silica.

Example 9: 4-(5-Amino-3-oxapent-1-yl) aminocarbonyl)phenylboronic acid (CPBA-BAEE)

After removal of dichloromethane by rotary evaporation from a $CH_2Cl_2$/DMF solution of NHS-CPBA (Example 3, 0.0013 mol), the resulting NHS-CPBA in solution in 8 ml DMF was filtered and added to a solution of bis-(2-aminoethyl)-ether (BAEE, 0.00106 mol) in 10 ml of 0.4M sodium-bicarbonate buffer, pH 8.5. The mixture was stirred and left to react overnight (approx. 12 hours) at ambient temperature. The reaction mixture was evaporated to dryness and the title compound isolated and purified by chromatography on silica.

Example 10: 4-((2-Aminoethyl)aminocarbonyl)- phenylboronic acid (CPBA-EDA)

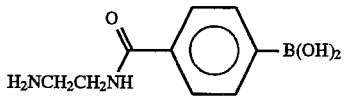

A newly filtered solution of HBT-CPBA (Example 2, 0.00121 mol) was added through a dropping funnel to a solution of 1,2-ethylenediamine (EDA, 0.00145 mol) in 1 ml pyridine. The mixture was stirred under nitrogen and left to react overnight (approx. 12 hours) at ambient temperature. The title compound was isolated and purified by chromatography on silica.

Example 11: 4-((2-Aminoethyl)aminocarbonyl)- phenylboronic acid (CPBA-EDA)

The procedure of Example 10 was repeated using a newly filtered solution of NHS-CPBA (Example 3, 0.00121 mol) instead of HBT-CPBA.

Example 12: 4-((3-Aminopropyl)aminocarbonyl) phenylboronic acid (CPBA-DAP)

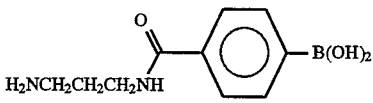

A newly filtered solution of HBT-CPBA (Example 2, 0.00106 mol in 1 ml DMF) was added through a dropping funnel to a solution of 1,3-diamino-propane (DAP, 0.00127 mol) in 1 ml pyridine. The mixture was stirred under nitrogen and left to react overnight (approx. 12 hours) at ambient temperature. The title compound was isolated and purified by chromatography on silica.

Example 13: 4-((3-Aminopropyl)aminocarbonyl) phenylboronic acid (CPBA-DAP)

The procedure of Example 12 was repeated using a newly filtered solution of NHS-CPBA (Example 3, 0.0121 mol) instead of HBT-CPBA.

Example 14: 4-((6-Aminohexyl)aminocarbonyl)- phenylboronic acid (CPBA-DAH)

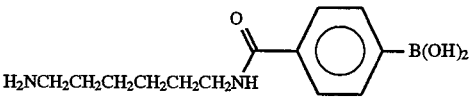

A newly filtered solution of HBT-CPA (Example 2, 0.00106 mol in 10 ml DMF) was added through a dropping funnel to a solution of 1,6-diamino-hexane (DAP, 0.00127 mol) in 1 ml pyridine. The mixture was stirred under nitrogen and left to react overnight (approx. 12 hours) at ambient temperature. The title compound was isolated and purified by chromatography on silica.

Example 15: 4-((6-Aminohexyl)aminocarbonyl)- phenylboronic acid (CPBA-DAH)

The procedure of Example 14 was repeated using a newly filtered solution of NHS-CPBA (Example 3, 0.0121 mol) instead of HBT-CPBA.

Example 16: 4-((4-Amino-4-carboxy-butyl) aminocarbonyl)phenylboronic acid (CPBA-ornithine)

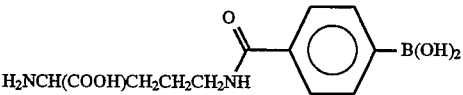

A newly filtered solution of HBT-CPBA (Example 2, 0.00042 mol in 4 ml DMF) was added through a dropping funnel to a solution of Nδ-t-Boc-L-ornithine (Boc-Orn, 0.0005 mol) in 2 ml of 0.4M sodium bicarbonate buffer, pH 8.5/10 ml DMF. The mixture was stirred and left to react overnight (approx. 12 hours) at ambient temperature. The reaction mixture was evaporated to dryness and the residue dissolved in 10 ml DMF. 5 ml of a solution comprising $CHCl_3$/trifluoroacetic acid (50/50) was then added to remove the amine-protecting Boc-group, and the deprotection was followed by TLC-analysis on silica in methanol:$NH_3$ (aq)–3:1. When deprotection was completed (<1 hour) the resulting title compound was isolated and purified by chromatography on silica.

Example 17: 4-((6-Aminohexyl)aminocarbonyl)-phenylboronic acid (CPBA-ornithine)

After removal of dichloromethane by rotary evaporation from a CH$_2$Cl$_2$/DMF-solution of NHS-CPBA (Example 3, 0.0010 mol), NHS-CPBA in solution in 5 ml DMF was filtered and added to a solution of Nδ-t-Boc-L-ornithine (Boc-Orn, 0.0005 mol) in 2 ml of 0.4M sodium bicarbonate buffer, pH 8.5/10 ml DMF. The mixture was stirred and left to react overnight (approx. 12 hours) at ambient temperature. The reaction mixture was evaporated to dryness and the residue dissolved in 10 ml DMF. 5 ml of a solution comprising CHCls/trifluoroacetic acid (50/50) was then added to remove the amine-protecting Boc-group, and the deprotection was followed by TLC-analysis on silica in methanol:NH$_3$ (aq)—3:1. When deprotection was completed (<1 hour) the resulting title compound was isolated and purified by chromatography on silica.

Example 18: Xylene-cyanole-phenylboronic acid conjugates (A) XC-DAPOL-CPBA

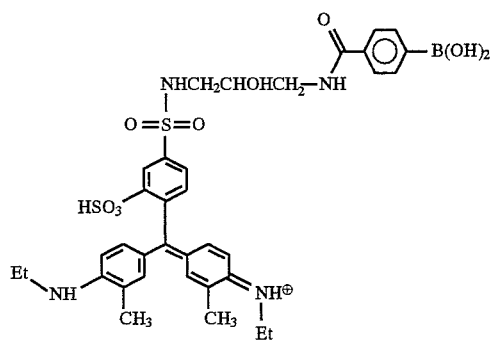

Purified CPBA-DAPOL (Example 4 or 5, 0.05 g, 0.000210 mol) was dissolved in 50 μl methanol before 1 ml of DMF and 10.5 ml of 0.1M sodium-bicarbonate buffer, pH 8.6 were added. Under constant stirring using a magnetic stirrer, Xylene-cyanole-SO$_2$Cl (139 mg, 0.00026 mol in 5 ml of methylcyanide) was added over a period of 5 minutes. The reaction mixture was left to react overnight (approx. 12 hours) at ambient temperature. The product, XC-DAPOL-CPBA, was purified twice on silica using pure methanol as solvent. The isolated dye-boronic acid derivative possess an absorption maximum at 616 nm, extinction coefficient =70 000 1/mol.cm.

(B) to (G) XC-"spacer"-CPBA

The procedure described for Example 18(A) is repeated using the compounds of Examples 6/7, 8/9, 10,11, 12/13, 14/15 and 16/17 instead of that of Examples 4/5.

Example 19 (Comparative)

Deboronation of a Xylene Cyanole-3-aminophenylboronic acid-conjugate

Chromatographically pure (>96%) Xylene Cyanole-3-aminophenylboronic acid-conjugate (synthesized and isolated as described in Example 2 of WO-92/08722) was dissolved in DMSO and then diluted to a final concentration of 1.9×10$^{-4}$ M in 100 mM sodium-bicarbonate-buffer/15% DMSO, pH 9.7 before being stored for 3 days at ambient temperature. After storage, the solution was chromatographed using reversed phase chromatography (RPC) on C1S-bonded silica. Two blue-dyed main fractions were isolated. On analytical RPC using a 20 mM ammonium acetate, pH7.0/methanol-gradient, the isolated dyed compounds eluted differently than the fresh Xylene Cyanole-3-aminophenyl boronic acid-conjugate. Elemental analysis showed no boron in the isolated compounds. These findings were confirmed by the results obtained using the method described in Example 7 of WO-92/08722. No signal response as a function of blood hemoglobin glycation was found, indicating the absence of active conjugate.

Example 20 (Comparative)

Deboronation of a Xylene Cyanole-3-aminophenylboronic acid-conjugate

Chromatographically pure (>96%) Xylene Cyanole-3-aminophenylboronic acid-conjugate (synthesized and isolated as described in Example 2 of WO-92/08722) was dissolved in DMSO and then diluted to a final concentration of 1.9×10$^4$ M using a buffer solution comprising 100 mM glycylglycine, 25 mM zinc-chloride, 0.07% Triton X-100, 10% DMSO, pH 9.7. The solution was stored at 4° C. for 14 days, and then chromatographed using reversed phase chromatography (RPC) on C18-bonded silica. Three blue-dyed compounds were isolated. Two of the isolated compounds (representing >70% of the blue dye intensity) eluted differently than the fresh Xylene Cyanole-3-aminophenyl boronic acid-conjugate on analytical RPC using a 20 mM ammonium acetate, pH 7.0/methanol-gradient. Elemental analysis showed no boron in these compounds. These findings were confirmed by the results obtained using the method described in Example 7 of W0-92/08722. No signal response as a function of blood hemoglobin glycation was found, indicating the absence of active conjugate in the isolated blue-dyed derivative.

Example 21

Stability of Xylene Cyanole-3-aminophenylboronic acid and the corresponding DAPOL-CPBA-conjugate stored in a neutral solution at 30° C./37° C.

Two identical solutions of XC dye-boronic acid-conjugates were made using for one Xylene Cyanole-3-aminophenylboronic acid produced and isolated as described in Example 2 of WO-92/08722 and for the other the corresponding Xylene Cyanole-DAPOL-CPBA conjugate produced and isolated as described in Example 18(A).

Solution I comrised:

Xylene Cyanole-3-aminophenyl boronic acid (XC-APBA, 2.3×10$^{-4}$ M), 100 mM glycinamide, 25mM zinc-chloride, 0.07% Triton X-100, 16% formamide, pH 7.5.

Solution II comprised:

Xylene Cyanole-DAPOL-CPBA (XC-DAPOL-CPBA, 2.3×10$^{-4}$ M), 100 mM glycinamide, 25 mM zinc-chloride, 0.07% Triton X-100, 16% formamide, pH 7.5.

Both solutions were stored at 30° C. for 14 days.

During storage the stability of these solutions was investigated by using them as working solutions of "dye-boronic acid conjugate" in the determination of glycohemoglobin as described below. Reduced availability of active conjugate, either resulting from deboronation or other degradative reactions on the dye-boronic acid conjugate during storage, was displayed as a malfunction of the assay in the determination of glycohemoglobin.

Measurement of glycohemoglobin in whole blood using Xylene Cyanole-boronic acid conjugate To test the effect of storage on solutions I and II, the incubated solutions were used separately to determine glycohemoglobin in whole blood samples, repeating the procedure at different times of storage. 2.5 µl of a whole blood sample was mixed with 150 µl of solution I or II, respectively. The whole blood sample was hemolyzed and a precipitate was formed. The precipitated hemoglobin was separated by filtration, and its reflectance measured at 685 and 470 nm by a reflectometer. The ratio of the reflectances at 685 and 470 nm was calculated, and the percentage of glycohaemoglobin to total haemoglobin was determined from a calibration curve obtained using standard solutions of known concentrations of haemoglobin and glycohaemoglobin.

Blood samples with known glycohemoglobin values were used in this study, and the resulting standard curve was compared with the curve obtained with corresponding freshly made dye-boronic acid conjugate solutions. If the concentration of active conjugate is reduced in the dye-boronic acid conjugate solution, a declining slope is observed. The effect on the slope was used as a measure of conjugate stability.

Already after storage for 6 days at 30° C., solution I showed a significant change in signal response as a function of blood hemoglobin glycation, whereas no significant negative effects were seen using solution II. Further incubation for 6 days resulted in a distinct drop in signal response using solution I, but still no detrimental effects were seen using solution II. After further incubation for 5 days (total=17 days), now at 37° C., still no negative effects were seen using solution II. At this time, the XC-APBA-conjugate in solution I showed almost no functionality. By visual inspection of the solutions during storage, it was also easy to observe a distinct decrease in color intensity in solution I as a function of time. The observed differences between solution I and II demonstrate the differences in stability of the two tested Xylene Cyanole (XC)-boronic acid conjugates.

Compared with the corresponding XC-APBA-conjugate, the XC-DAPOL-CPBA-conjugate showed superior stability under all conditions tested.

Example 22: Phthalocyanine-labelled boronic acid conjugate

Chloroaluminium phthalocyanine tetrasulphonate (100 mg, $1.12 \times 10^{-4}$ mol) is dried overnight at 100° C. Phosphorus oxychloride (410 µl, $4.48 \times 10^{-3}$ mol) is added and the mixture is incubated at ambient temperature under exclusion of moisture. After 24 hours at this temperature, unreacted phosphorus oxychloride is removed by bulb-bulb distillation.

The remaining solid phthalocyanine sulphonyl chloride is washed with chloroform and dried under reduced pressure and exclusion of moisture. 500 µl dry DMF is added to solubilize the phthalocyanine sulphonylchloride. Immediately thereafter 3 ml of 0.3 M $NaHCO_3$ solution pH 8.5, containing $1.3 \times 10^{-4}$ mol CPBA-DAPOL (prepared as described in Example 4) is added, and the reaction mixture is left to react for a minimum of 2 hours at constant pH. The boronic acid conjugates are isolated by reversed phase chromatography, mainly in the form of mono(phenyl boronic acid)—functionalized dye.

Example 23: Cyanine dye—boronic acid conjugate

Phosphorus oxychloride (470 µl, $5.13 \times 10^{-3}$ mol) is added to the cyanine dye 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide, inner salt, sodium salt (commercially known as IR 125 or indocyanine green) (100 mg, $1.29 \times 10^{4}$ mol) and the resulting mixture is incubated at ambient temperature under exclusion of moisture for 24 hours. Unreacted phosphorus oxychloride is removed by bulb-bulb distillation. The IR-125 sulphonyl chloride is extracted into chloroform, and the extract is washed five times with 1 ml portions of cold water and then evaporated to dryness under reduced pressure and exclusion of moisture.

The resulting solid material is immediately solubilized in DMF (500 µl), to which solution is added 3 ml of 0.3 M $NaHCO_3$ solution, pH 8.5, containing $1.1 \times 10^{-4}$ mol CPBA-DAPOL (prepared as described in Example 4) and the reaction mixture is left to react for a minimum of 2 hours at constant pH. The boronic acid conjugates are isolated by reversed phase chromatography, mainly in the form of mono(phenyl boronic acid)-functionalized dye.

Example 24: Cyanine dye—boronic acid conjugate

To the reactive succinimidyl ester-cyanine dye Cy5.18 ($1.3 \times 10^{-7}$ mol) are added 1.5, $10^{-4}$ mol CPBA-DAPOL (prepared as described in Example 4) in 0.5 ml 0.1M sodium carbonate/sodium bicarbonate buffer (pH 9.3), with subsequent thorough mixing. The mixture is incubated under constant stirring at ambient temperature for 4 hours, and the phenyl boronic acid conjugate finally isolated by reversed phase chromatography.

Example 25: Cyanine—boronic acid-conjugate

The methyl ester of the cyanine dye commercially known as IR 132 in dioxane, is transformed into its dicarboxylic acid analogue by titration with aqueous hydroxide (LiOH) using equimolar amounts of ester and base.

To 100 mg of the carboxylic acid containing cyanine dye (1.1E-4 mol) is added 450 µl of phosphorus oxychloride (5.13E-3 mol) and the mixture is incubated at ambient temperature with the exclusion of moisture for 24 hours. The dark solution is poured over crushed ice, left for 5 minutes and the IR-132-carboxylic acid-chloride extracted into 40 ml of chloroform.

The chloroform extract is washed five times with 5 ml of ice-cold water and finally stored over anhydrous $Na_2SO_4$. Before being used further the dry chloroform-acid chloride extract is evaporated to dryness under reduced pressure and with the exclusion of moisture. The solid material is dissolved in 2 ml of dry methylene chloride and then $1.5 \times 10^{-4}$ mol of CPBA-DAPOL (prepared as described in Example 4) dissolved in 3 ml of 0.3 M $NaHCO_3$ solution, pH 8.5, is added. The reaction mixture is left to react for a minimum of 2 hours at constant pH and the boronic acid conjugates are isolated by reverse phase chromatography.

We claim:

1. Labelled boronic acid compound of formula

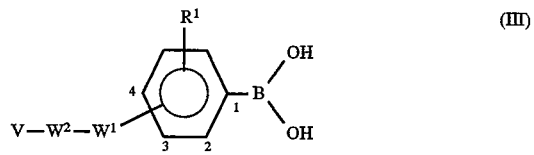

(III)

(wherein V is a reporter moiety;

$W^2$ is a bond or an organic linker moiety;

$W^1$ is a $*SO_2NR^2$, $*CONR^2$ or $*CH_2N{\oplus}R^2{}_2$ group bound at the *-marked atom to the phenyl ring;

$R^1$ is hydrogen or an electron withdrawing substituent group; and each $R^2$ independently is hydrogen or an optionally hydroxylated and optionally $C_{1-6}$-alkoxylated $C_{1-6}$-alkyl group) and salts thereof.

2. Compounds as claimed in claim 1 wherein $W^1$ is a $SO_2NR^2$ or $CONR^2$ group attached to the phenyl ring at the 4-position thereof.

3. Compounds as claimed in claim 1 wherein $W^1$ is a $SO_2NR^2$ or $CONR^2$ group attached to the. phenyl ring at the 2, 3, 5 or 6-position thereof.

4. Compounds as claimed in claim 1 wherein $W^1$ is a $CH_2N\oplus R_2{}^2$ group attached to the phenyl ring at the 3 or 5 position thereof.

5. Compounds as claimed in claim 1 wherein $W^1$ is a $CH_2N\oplus R_2{}^2$ group attached to the phenyl ring at the 2 4 or 6-position thereof.

6. Compounds as claimed in claim 1 wherein $R^1$ denotes an $SO_2H$, $CO_2H$ or $NO_2$ group attached at the 3 or 5 position of the phenyl ring.

7. Compounds as claimed in claim 1 wherein $R^1$ denotes an $SO_2H$, $CO_2H$ or $NO_2$ group attached at the 2, 4 or 6-positions of the phenyl ring.

8. Compounds as claimed in claim 1 wherein $W^2$ is a group of formula IV

(wherein each n is independently an integer having a value of 1 to 6, m is 0 or an integer having a value of 1 to 5, $X^1$ is a bond, an oxygen or sulphur atom, a $NR^2$ group, or a carboxy or carbonyl group, each $X^2$ is independently an oxygen or sulphur atom or an $NR^2$ group, $R^2$ is as defined in claim 1, and each $R^3$ independently is hydrogen, hydroxy, formyl, carboxy, or optionally hydroxylated and/or $C_{1-6}$-alkoxylated $C_{1-6}$-alkyl, or a group $CHR_3$ represents a carbonyl group).

9. Compounds as claimed in claim 8 wherein $W^2$ is selected from the group consisting of:

—NH—CH$_2$—CHOH—CH$_2$—
—NH—CH$_2$CH$_2$—NH—CH$_2$CH$_2$—
—NH—CH$_2$CH$_2$—O—CH$_2$CH$_2$—
—NH—CH$_2$CH$_2$—
—NH—CH$_2$CH$_2$CH$_2$—
—NH—CH$_2$CH$_2$CH$_2$CH$_2$—
—NH—CH$_2$CH$_2$CH$_2$CH(COOH)—
NH—CH$_2$CHOH—
—NH—CH$_2$CH(COOH)—
—NH—CH$_2$—NH—CH$_2$—
—NH—CH$_2$CH$_2$CH$_2$CH$_2$CH$_2$CH$_2$—
—NH—CH$_2$CH$_2$CH$_2$CH$_2$CH$_2$—
—NH—CH$_2$—O-CH$_2$—
—NH—CH$_2$—O—CH$_2$—O—CH$_2$—
—NH—CH$_2$CH$_2$—O—CH$_2$CH$_2$—O—CH$_2$CH$_2$—
—NH—CH(COOH)CH$_2$CH$_2$—
—NH—CH(COOH)CH$_2$CH$_2$CH$_2$
—NH—CH$_2$CH(COOH)CH(COOH)—
—NH—CH$_2$CHOHCHOH— and
—NH CH$_2$CH(CHO)CH(CHO)— groups.

10. Compounds as claimed in claim 1 wherein V is a chromophore or fluorophore.

11. Compounds as claimed in claim 10 wherein V has an absorption maximum in the range 600–1000 nm.

12. Compounds as claimed in claim 10 wherein V is an azine, triarylmethine, phthalocyanine or cyanine dye.

13. Compounds as claimed in claim 12 wherein V is a xylene-cyanole dye.

14. Compounds as claimed in claim 1 being compounds of formula (V)

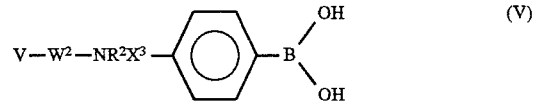

where V and $R^2$ are as defined in claim 1, $X^3$ is a CO or $SO_2$ group, and $W^2$ is a group of formula IV

wherein each n is independently an integer having a value of 1 to 6;

m is 0 or an integer having a value of 1 to 5;

$X^1$ is a bond, an oxygen or sulfur atom, a $NR^2$ group, or a carboxy or carbonyl group, each $X^2$ is independently an oxygen or sulphur atom or an $NR^2$ group, $R^2$ is as defined in claim 1, and each $R^3$ independently is hydrogen, hydroxy, formyl, carboxy, or optionally hydroxylated and/or $C_{1-6}$-alkoxylated $C_{1-6}$-alkyl, or a group $CHR^3$ represents a carbonyl group.

15. Compounds as claimed in claim 1 being compounds of formula VI

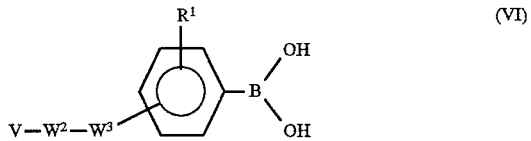

(where V, $R^1$ and $W^2$ are as defined in claim 1, and $W^3$ is NHCO or $SO_2NH$) and salts thereof.

16. Compounds as claimed in claim 1 being compounds of formula VII

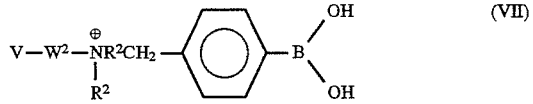

(where V, $W^2$ and $R^2$ are as defined in claim 1) and salts thereof.

17. Compound of formula VIII

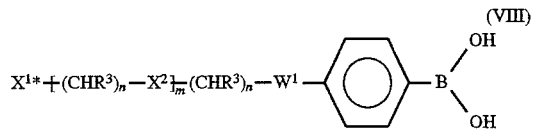

(where $X^2$, $R^1$, $R^3$, n m and $W^1$ are as defined in claim 8 and $X^{1*}$ is a reactive functional group) and salts thereof.

* * * * *